United States Patent
Voermans et al.

(10) Patent No.: US 11,641,803 B2
(45) Date of Patent: May 9, 2023

(54) METHOD AND SYSTEM FOR PICKING UP AND COLLECTING PLANT MATTER

(71) Applicant: RIJK ZWAAN ZAADTEELT EN ZAADHANDEL B.V., De Lier (NL)

(72) Inventors: Wilhelmus Petrus Adrianus Roeland Voermans, De Lier (NL); Mark Van Den Berg, De Lier (NL); Kevin Cornelis Adrianus Gerardus Verbocht, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 734 days.

(21) Appl. No.: 16/377,794

(22) Filed: Apr. 8, 2019

(65) Prior Publication Data
US 2019/0281765 A1    Sep. 19, 2019

Related U.S. Application Data

(63) Continuation-in-part of application No. PCT/NL2017/050658, filed on Oct. 6, 2017.

(30) Foreign Application Priority Data

Oct. 10, 2016    (NL) ...................................... 2017599

(51) Int. Cl.
*G05B 15/00*    (2006.01)
*G05B 19/00*    (2006.01)
(Continued)

(52) U.S. Cl.
CPC .............. *A01D 46/30* (2013.01); *A01H 4/001* (2013.01); *B25J 9/1679* (2013.01); *B25J 9/1697* (2013.01);
(Continued)

(58) Field of Classification Search
CPC ........ A01D 46/30; A01H 4/001; A01H 4/006; C12M 41/48; B25J 11/00; B25J 9/1679;
(Continued)

(56) References Cited

U.S. PATENT DOCUMENTS 6,351,690 B1 *    2/2002    Lenz ................... G01N 35/0099
                                                           422/400
10,552,951 B2 *   2/2020    Barrasso ................ H05B 45/20
(Continued)

FOREIGN PATENT DOCUMENTS

CN          104438095 A  *  3/2015
EP          1498025 A2       1/2005
(Continued)

OTHER PUBLICATIONS

L. E. Weiss, et al., Dynamic Sensor-Based Control of Robots with Visual Feedback, IEEE Journal of Robotics and Automation (Oct. 1987) vol. RA-3, No. 5, p. 404-417.
(Continued)

*Primary Examiner* — Harry Y Oh
(74) *Attorney, Agent, or Firm* — Duane Morris LLP; Thomas J. Kowalski; Deborah L. Lu

(57) ABSTRACT

The invention relates to a method and system for picking up and collecting plant matter, in particular plant embryos. To pick up the plant matter, a pick-up unit is used that is mounted to a robotic arm. According to the invention, two separate imaging steps are performed at two different positions of the pick-up unit. The first imaging step is performed to identify an isolated piece of plant matter. The second imaging step is performed when the pick-up unit is at a confirming position and enables a verification of whether a piece of plant matter has been picked up or not. The confirming position is in between the position of the pick-up
(Continued)

unit for picking up plant matter and the position for depositing plant matter in suitable receptacles.

17 Claims, 7 Drawing Sheets

(51) Int. Cl.

| | | |
|---|---|---|
| A01D 46/30 | (2006.01) | |
| B25J 9/16 | (2006.01) | |
| B25J 11/00 | (2006.01) | |
| G06Q 50/02 | (2012.01) | |
| G01N 1/04 | (2006.01) | |
| A01H 4/00 | (2006.01) | |
| C12M 1/36 | (2006.01) | |
| G01N 1/00 | (2006.01) | |
| G06V 20/10 | (2022.01) | |
| G01N 35/00 | (2006.01) | |

(52) U.S. Cl.
CPC .............. *B25J 11/00* (2013.01); *C12M 41/48* (2013.01); *G01N 1/00* (2013.01); *G01N 1/04* (2013.01); *G06Q 50/02* (2013.01); *G06V 20/188* (2022.01); *A01H 4/006* (2013.01); *G01N 35/0099* (2013.01); *G05B 2219/00* (2013.01); *G05B 2219/45063* (2013.01); *G06T 2207/30188* (2013.01)

(58) Field of Classification Search
CPC ........... B25J 9/1697; G01N 1/00; G01N 1/04; G01N 35/0099; G05B 2219/00; G05B 2219/45063; G06T 2207/30188; G06Q 50/02; G06K 9/00657

See application file for complete search history.

(56) References Cited

U.S. PATENT DOCUMENTS

| | | | | |
|---|---|---|---|---|
| 2005/0108931 | A1* | 5/2005 | McKinnis | A01C 11/00 47/10 |
| 2005/0114918 | A1* | 5/2005 | Hirahara | A01H 4/006 800/278 |
| 2009/0251697 | A1* | 10/2009 | Cutillas | H01S 5/02325 356/400 |
| 2013/0110280 | A1* | 5/2013 | Folk | B25J 9/1697 700/215 |
| 2016/0068793 | A1* | 3/2016 | Maggiore | B29C 64/227 435/289.1 |
| 2016/0114977 | A1* | 4/2016 | Li | B23P 19/001 193/44 |
| 2017/0143429 | A1* | 5/2017 | Richmond | A61B 5/064 |

FOREIGN PATENT DOCUMENTS

| | | |
|---|---|---|
| EP | 2543482 A1 | 1/2013 |
| WO | 0113702 A2 | 3/2001 |

OTHER PUBLICATIONS

Peter I. Corke, Visual Control of Robot Manipulators—A Review, Visual Servoing (Jan. 1, 1993) http://reference.kfupm.edu.sa/ Retrieve from the Internet: URL:HTTP://reference.kfupm.edu.sa/content/v/i/visual_control_of_robot_manipulators_569323.pdf.
International Search Report and Written Opinion dated Jan. 10, 2018 in Int'l Application No. PCT/NL2017/050658.

* cited by examiner

Fig. 6D
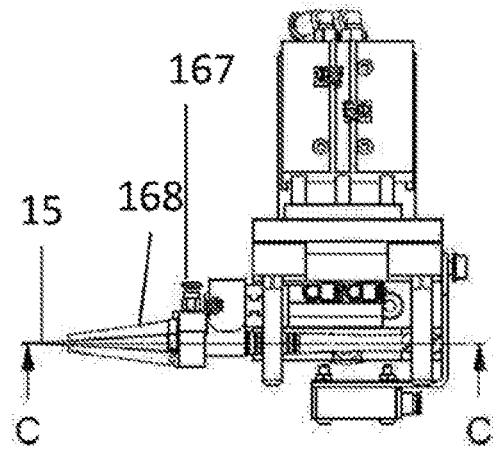
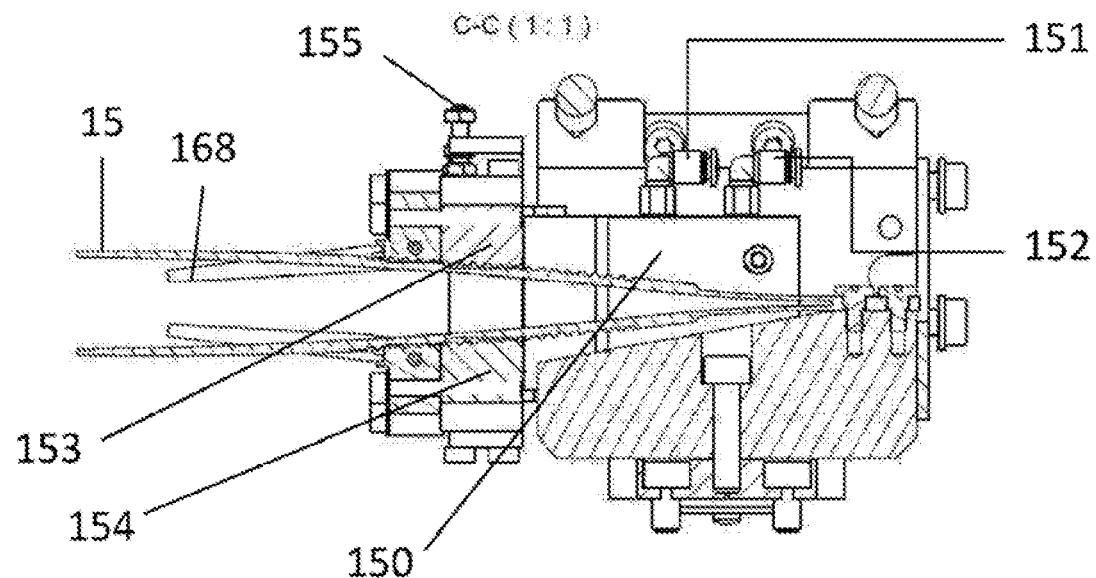
Fig. 6E ered in the captured first optical image. Then, a robotic arm having a pick-up unit mounted thereon is controlled to move the pick-up unit to a position in which it is able to pick up the isolated piece of plant matter. A picking up action is performed next for picking up the isolated piece of plant matter using the pick-up unit. As a next step, the robotic arm is controlled to move the pick-up unit to a predefined confirming position, and a second optical image is captured in which a part associated with the picked-up piece of plant matter does not overlap with a part, if any, in the second optical image that is associated with the receptacle.
METHOD AND SYSTEM FOR PICKING UP AND COLLECTING PLANT MATTER

RELATED APPLICATIONS AND INCORPORATION BY REFERENCE

This application is a continuation-in-part application of international patent application Ser. No. PCT/NL2017/050658 filed Oct. 6, 2017, which published as PCT Publication No. WO 2018/070866 on Apr. 19, 2018, which claims benefit of NL patent application Ser. No. 2017599 filed Oct. 10, 2016.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to a method and system for picking up and collecting plant matter, in particular plant embryos.

BACKGROUND OF THE INVENTION

Plant embryos form an important tool in modern contemporary plant breeding leading to hybrid plants. In order to speed up the creation of the required genetically pure lines, the use of doubled haploids (DHs) has become a very valuable tool. In addition, DHs also help greatly to evaluate and monitor difficult traits such as those that are encoded by multiple genes/alleles.

The production and the use of DHs in breeding crop plants is well known for many plant species. Thus far, DHs can be obtained from spores of the male (androgenesis) or female (gynogenesis) organs.

Androgenesis is defined as a set of biological processes leading to the development of individuals derived from the nuclei of male spores. Spores from the male organs are called microspores and the in vitro cultures are called microspore cultures. Typical microspore cultures are well established in Brassica since a long time. Spores from the female organs are called megaspores, and the in vitro culture of these spores is commonly named gynogenesis. Gynogenesis is a well established technique for e.g. sugar beet and also cucumber.

Above described techniques result in the formation of plant embryos, through a process called embryogenesis. These embryos develop from one single cell into a plant, when grown under special conditions and provided with appropriate growth media. Depending on the plant species, developing embryos are grown in liquid or on solid growth media. When the embryos have reached the desired growth stage, they might be singulated.

In many situations, it may be desirable to automate a process for picking up and collecting the plant embryos. Typically, the embryos are available in relatively large liquid containing reservoirs. To isolate the embryos, the content of the reservoir is poured into a receptacle, typically having a relatively large surface allowing the embryos to spread over the surface. Then, a user may pick up isolated embryos and place them in respective compartments, such as test tubes, for further analysis or processing. This manual process is very labour intensive, and it is therefore desirable to automate this picking up process.

Automated methods for picking up and collecting plant matter such as plant embryos are known from the prior art.

For instance, from US 2005/0114918, a system and method of embryo delivery for manufactured seeds is known in which a robotic arm with a pick-up head which may comprise micro-tweezers is used. In this system, an imaging system is present for obtaining attributes of the plant embryos. Plant embryos which are determined to be suitable for germination are detected, and are then specifically oriented one at a time by movement of a positioning table to a retrieval position. In the retrieval position, the embryos are picked up by the pick-up head. It is also mentioned that a robotic housing capable of moving in multiple directions may be used in conjunction with or in the absence of a positioning table.

Another system is known from EP 1 498 025, which discloses an automated system and method for harvesting and multi-stage screening of plant embryos. In this system as well, the embryos may be imaged by a camera, and the image is used to ascertain the embryo's shape and size. Undesirable embryos may be removed. Desirable embryos may be transferred onto a receiving surface, for instance by picking them up using a vacuum tip end.

Citation or identification of any document in this application is not an admission that such document is available as prior art to the present invention.

SUMMARY OF THE INVENTION

There is a continuing demand for processing larger quantities of embryos. This requires that the amount of time required for picking up and collecting a plant embryo is reduced. At the same time, for some applications it has to be guaranteed that each compartment, e.g. test tube, is not empty but may comprise a single plant embryo.

It is an object to provide a more efficient and more precise method for picking up and collecting plant matter, in particular plant embryos, while still providing sufficient certainty that the plant embryos are deposited in the intended compartments.

This object may be achieved by a method according to the invention, which may comprise the steps of capturing a first optical image, being an image of at least one piece of plant matter, such as a plant embryo, arranged in a receptacle. Next, an isolated piece of plant matter is detected in the captured first optical image. Then, a robotic arm having a pick-up unit mounted thereon is controlled to move the pick-up unit to a position in which it is able to pick up the isolated piece of plant matter. A picking up action is performed next for picking up the isolated piece of plant matter using the pick-up unit. As a next step, the robotic arm is controlled to move the pick-up unit to a predefined confirming position, and a second optical image is captured in which a part associated with the picked-up piece of plant matter does not overlap with a part, if any, in the second optical image that is associated with the receptacle.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 6A-6E present different views of the embodiment shown in FIG. 5.

DETAILED DESCRIPTION OF THE INVENTION

Figure 1:
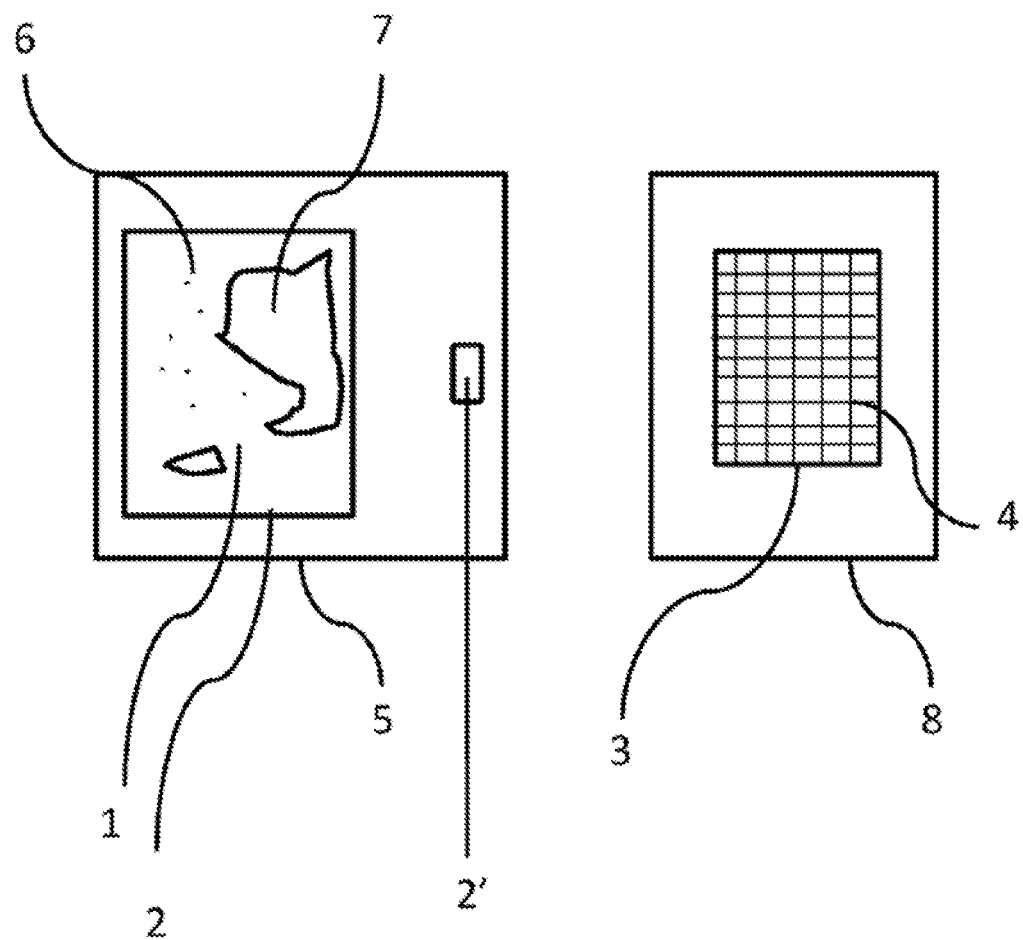
FIG. 1 shows a top view illustrating a receptacle and tray to be used in the invention.

It is an object to provide a more efficient and more precise method for picking up and collecting plant matter, in particular plant embryos, while still providing sufficient certainty that the plant embryos are deposited in the intended compartments.

This object may be achieved by a method according to the invention, which may comprise the steps of capturing a first optical image, being an image of at least one piece of plant matter, such as a plant embryo, arranged in a receptacle. Next, an isolated piece of plant matter is detected in the captured first optical image. Then, a robotic arm having a pick-up unit mounted thereon is controlled to move the pick-up unit to a position in which it is able to pick up the isolated piece of plant matter. A picking up action is performed next for picking up the isolated piece of plant matter using the pick-up unit. As a next step, the robotic arm is controlled to move the pick-up unit to a predefined confirming position, and a second optical image is captured in which a part associated with the picked-up piece of plant matter does not overlap with a part, if any, in the second optical image that is associated with the receptacle.

Thus, the method includes two separate imaging steps. In the first imaging step, the presence of an isolated piece of plant matter is detected, and if an isolated piece of plant matter is found, the position thereof is determined. In the second imaging step, it is checked whether a piece of plant matter was indeed picked up. To be able to properly see the picked-up piece of plant matter, the pick-up unit is moved to a confirming position in which the picked-up piece can be seen separate from other pieces of plant matter that are still arranged in the receptacle.

When a piece of plant matter has been picked up, it can be deposited in a respective compartment, whereas if no piece of plant matter has been picked up, the same intended isolated piece of plant matter or another piece of isolated plant matter can be picked up. As the plant matter is typically arranged in a liquid held in the receptacle, it may be preferable to pick up a different piece of isolated plant matter as the process of picking up plant matter may have changed the position and/or orientation of the originally intended piece of isolated plant matter.

By checking whether a piece of plant matter has been picked prior to depositing such a piece in a compartment such as a test tube or another receiving surface, it becomes possible to more quickly react to situations in which a piece of plant matter has not been picked up. For instance, the distance that needs to be covered by the robotic arm and more in particular the pick-up unit can be reduced considerably by using the predefined confirming position. As a result, the throughput can be increased considerably.

It is preferable if the confirming position lies on or close to a path from the receptacle to the compartment, wherein the compartment is preferably part of a tray which may comprise a plurality of compartments. More in particular, it is preferable if the confirming position is close to the receptacle provided that the imaging of the picked up piece of plant matter is not disturbed by either the receptacle or the other pieces of plant matter contained therein. A situation in which a piece of plant matter that is still in the receptacle is misinterpreted as being a picked-up piece of plant matter should be avoided.

The receptacle may be visible in the second optical image, for example only partially. In this case the method may further comprise detecting the further isolated piece of plant matter from the second optical image. This means that the second imaging step for confirming that a current piece of plant matter has been picked up is simultaneously the first imaging step for the detecting the presence of a further isolated piece of plant matter. This is advantageous for reasons of efficiency, and has the further advantage that while the pick-up unit is in the predetermined confirming position, an unobstructed view of the receptacle can be obtained. However, the detecting of the further isolated piece of plant matter may also be done using the already obtained first optical image. Use of several images is also an option, as is the use of a continuous image feed.

The method may comprise capturing a new first optical image for detection of a piece of plant matter to be picked up next when the pick up unit does not obstruct a view of the receptacle in the new first optical image. For instance, the new first optical image may captured when the pick-up unit is at or moving towards the position for depositing a picked-up piece of plant matter.

The two imaging steps may be performed by two different cameras. However, advantageously, a same optical camera may be used for obtaining the first and second optical images. This camera is preferably positioned in such a way that it has a good view of both the receptacle and of the predefined confirming position. However, it may be possible for the camera to move from a first to a second imaging position. Also, the optical camera may perform a zooming function prior to recording the second optical image, as more precision may be desired.

The detecting of an isolated piece of plant matter or the detecting of a further isolated piece of plant matter may comprise finding an isolated piece of plant matter in the first or second optical image, comparing at least one of a size, colour, and shape to predetermined criteria, and determining that the isolated piece of plant matter should be picked up if the at least one of a size, an orientation, colour, and shape meets the predetermined criteria. By comparing with predetermined criteria, plant matter that is unsuitable for further processing, for instance due to abnormal growth or because the plant matter relates to a different type of plant, can be excluded.

The method may comprise controlling the robotic arm to rotate the pick-up unit during and/or after a movement to the predefined confirming position, to allow a better view of the picked-up piece of plant matter, if present. During the picking up of the plant matter, the pick-up unit will likely be located substantially between the camera and the receptacle, therefore potentially obscuring a view of the picked-up piece of plant matter. By controlling the robotic arm to rotate the pick-up unit, detection of the picked-up piece of plant matter, if present, may be improved. Preferably the pick-up unit is rotated to provide an unobstructed view of the picked-up piece of plant matter, if present.

The method may comprise a step of detecting an orientation of the isolated piece of plant matter or the further isolated piece of plant matter in the first and/or second optical image, and orienting the pick-up unit accordingly prior to performing the picking up action. This allows the pick-up unit to more reliably picking up the plant matter with less of a chance of damage. For instance, it may be advantageous to pick-up plant matter by a less fragile part such as, for example, the (primary) root, the hypocotyl or the stem.

If no isolated piece of plant matter is detected in the first and/or second optical image, a blowing unit may be moved along a pre-set trajectory while directing a pressurized gaseous medium, such as air, toward the receptacle. This may break up clusters of plant matter in which several pieces of plant matter are clustered close together, and may make it possible to isolate further pieces of plant matter. The skilled person will be able to assess a necessitated blowing strength as well as possible trajectories.

After the step of moving the blowing unit along a pre-set trajectory, the blowing unit may be moved to a position wherein a new first or second optical image can be obtained having a substantially unobstructed view of the receptacle; and detecting whether there are any isolated pieces of plant matter in the receptacle using the first and/or second optical image. In this manner it may be assessed whether the blowing unit moving along a pre-set trajectory managed to isolate further pieces of plant matter. If no isolated pieces are detected in the last step, the blowing unit may be moved along a different pre-set trajectory while directing the pressurized gaseous medium toward the receptacle. After this, it may again be assessed, by obtaining a new first or second optical image, if the movement of the blowing unit while directing a pressurized gaseous medium toward the receptacle was successful in isolating further pieces of plant matter. This process may be repeated a number of times, for instance three times with three different trajectories. If after a pre-set number of repetitions it is still the case that no isolated pieces of plant matter may be detected, a warning signal may be transmitted to an operator. This may for instance be at least one of an auditory signal and a visual signal. The operator may thus be prompted to provide a further receptacle containing plant matter. The skilled person will be able to automate this step as well if desired.

In the above, the step of directing pressurized gaseous medium toward the receptacle may involve blowing the pressurized gaseous medium downward at a substantially straight angle with respect to a plan defined by the bottom of the receptacle. This may be most efficient at breaking up clusters of plant matter.

Once there are no longer any free compartments in the tray, the tray may be replaced. While this may be done manually, it is preferably performed using a gripping unit for replacing the tray. Advantageously, the blowing unit and/or the gripping unit may be mounted to the same robotic arm as the pick-up unit. Moreover, the movement of the blowing unit and/or gripping unit can be controlled by controlling the robotic arm. Additionally or alternatively, the blowing unit and/or gripping unit are integrated in the pick-up unit.

It is a further object of the invention to provide a more efficient and/or precise system for picking up plant matter, such as plant embryos and for collecting the picked-up plant matter in a tray having at least one compartment. This object may be achieved by a system according to the invention, which may comprise a surface whereupon a receptacle containing at least one piece of plant matter may be provided. The system further may comprise a robotic arm provided with a pick-up unit configured to pick-up a piece of plant matter, wherein the robotic arm is able to move the pick-up unit for picking up a piece of plant matter from the receptacle, to move the pick-up unit to a predefined confirming position for confirming the picking up of a piece of plant matter, and to move the pick-up unit for depositing a picked-up piece of plant matter into a respective compartment of the tray.

The system of the present invention also may comprise a camera system which may comprise an optical camera, said system being configured for capturing a first optical image being an image of at least one piece of plant matter arranged in a receptacle, and for capturing a second optical image in which a part associated with the picked-up piece of plant matter does not overlap with a part, if any, that is associated with the receptacle. The camera system preferably comprises a single camera for capturing the first and second optical images.

The system may comprise a controller configured for detecting an isolated piece of plant matter in the first optical image, controlling the robotic arm to move the pick-up unit to a position in which the unit can pick-up the detected isolated piece of plant matter, controlling the pick-up unit to pick-up the detected isolated piece plant matter, controlling the robotic arm to move the pick-up unit to a predefined confirming position, confirming the presence of a picked-up piece of plant matter in the second optical image, controlling the robotic arm and the pick-up unit to deposit the picked up piece of plant matter in a respective compartment if the picked up piece of plant matter is visible in the second optical image, or controlling the robotic arm to move the pick-up unit to a position in which it is able to pick up a further isolated piece of plant matter if no picked up piece of plant matter is visible in the second optical image.

The system described above is suitable and/or configured for performing the method of the invention.

The system may comprise a first light source configured for emitting light through the surface from a side of the surface opposite to a side of the surface where the receptacle is or is to be placed, wherein the receptacle is provided between the camera system and the light source, said light source preferably emitting red light. This may increase the visibility of the isolated pieces of plant matter, for instance by increasing the contrast of the image. The light source may emit red light, as this has been shown to advantageously increase the visibility of the plant matter, which tends to be green.

The system may further comprise a second light source, wherein the pick-up unit, when at the predefined confirming position, is located between the camera system and a second light source that is configured for emitting light to the pick-up unit, said light source preferably emitting red light. This allows the contrast of a picked-up piece of plant matter to be improved.

The first light source can be the second light source. In other words, a single light source is used for emitting light to the receptacle and the pick-up unit.

The surface may comprise a first transparent region on which the receptacle is to be placed and a second transparent region, spaced apart from the first transparent region, wherein the first light source is configured for emitting light through the first transparent region, and wherein the second light source is configured for emitting light through the second transparent region. The first transparent region is substantially the same size as the receptacle and the receptacle is provided thereon. The receptacle is then placed on the first transparent region through which the receptacle itself is illuminated. Because the first transparent region has substantially the same size as the receptacle, little to no light is transmitted to the camera system without having passed through the receptacle. This may be advantageous as an unimpeded light source outside the receptacle may negatively affect the first image. The second transparent region may be much smaller, which is suitable for illuminating the picked-up piece of plant matter, if present, when the pick-up unit is in the predetermined confirming position.

The pick-up unit may comprise a pair of tweezers suitable for picking up an isolated piece of plant matter, wherein the tweezers are part of the pick-up unit. Tweezers suitable for picking up pieces of plant matter are known from the art and will be familiar to the skilled person. The tweezers may for instance be pneumatically actuated tweezers, although alternatives will be known to the skilled person.

The pick-up unit may be moved in a plurality of directions by the robotic arm. This allows for very precise movement of the pick-up unit, which makes it possible to pick up very small pieces of plant matter. This also allows for the positioning of the pick-up unit in such a way that a potentially picked up piece of plant matter may be properly and efficiently detected. This may also help the depositing of the piece of plant matter in the compartment of the tray.

The pick-up unit can be pivotally mounted to an end of the robotic arm to allow rotation of the pick-up unit relative to the end of the robotic arm.

The system may further comprise a blowing unit suitable for directing a pressurized gaseous medium at the receptacle. As described above, in the absence of isolated pieces of plant matter, this may be employed to isolate pieces of plant matter from clusters of pieces of plant matter. The blowing unit is preferably controlled by the controller.

The system may further comprise a gripping unit suitable for gripping the tray, as the tray may need to be periodically replaced when all compartments contain a piece of plant matter. To make the process as efficient as possible, it is desirable to also automate this replacement of the tray. The gripping unit is preferably controlled by the controller.

The blowing unit and/or the gripping unit may be mounted to the same robotic arm as the pick-up unit, and the movement of the blowing unit and/or gripping unit may be controlled by controlling the robotic arm, to make the system as compact as possible. This is desirable as, when taking a first optical image of the receptacle, an unobstructed view is advantageous. The blowing unit and/or the gripping unit may be incorporated in the pick-up unit.

The present invention also provides a pick-up unit that is configured as the pick-up unit defined above.

Figure 2:
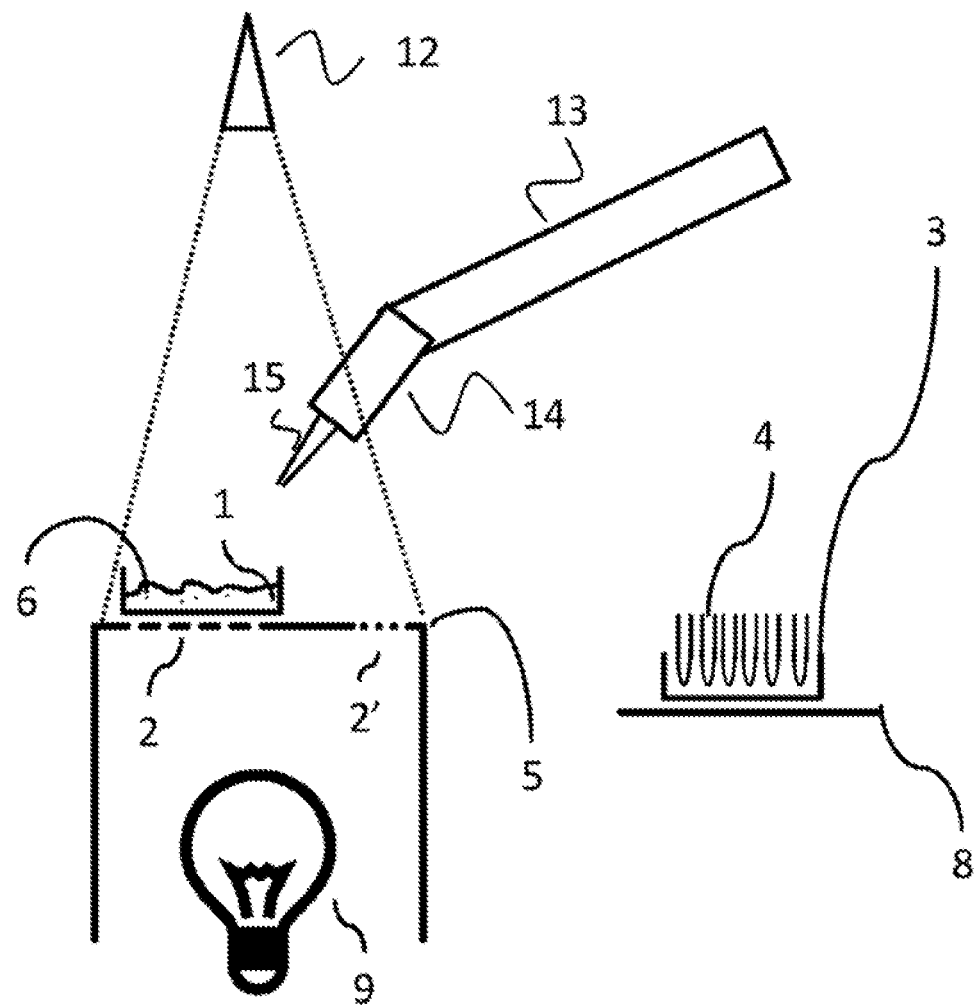
FIG. 2 is a side view illustrating a receptacle, tray, and robotic arm to be used in the invention.

In FIG. 1, a top view is shown of a receptacle 1 and tray 3 to be used in the invention, whereas FIG. 2 shows a corresponding side view. In FIG. 1, the robotic arm and the pick-up unit affixed thereon have been omitted to offer a clear view. Receptacle 1 contains clusters 7 of plant matter as well as isolated pieces 6 of plant matter, floating in a suitable liquid. In what follows, it will be assumed that the pieces of plant matter are plant embryos, but the invention is also suitable for the picking up of other types of pieces of plant matter.

Tray 3 may comprise a plurality of compartments 4, depicted as test tubes in FIG. 2. Each compartment 4 is suitable for receiving a respective picked-up piece of plant matter. While tray 3 is displayed as a grid, compartments 4 may also be distributed in a different manner, and the displayed number of compartments 4 should not be taken as limitative.

Receptacle 1 is provided on a support surface 5 such as a table, see FIG. 2. Surface 5 is provided with a first transparent region 2, located underneath receptacle 1, and a second transparent region 2'. Transparent regions 2 and 2' are indicated with dashed lines to make clear that they let through at least a part of the light emitted by a light source 9 that is arranged underneath surface 5. Here, light source 9 is abstracted as a light bulb but may be embodied as any type of light source, preferably one emitting red light, or as a combination of light sources. Light source 9, which preferably emits red light, allows for efficient detection of isolated embryos. Red is preferred since embryos and other plant matter tends to be green, and enhanced contrast may make it easier to detect isolated pieces.

While both receptacle 1 and transparent regions 2, 2' are depicted as having a rectangular shape, other shapes are of course also possible. Furthermore, the size of receptacle 1 and the size of transparent region 2 are preferably substantially equal. This may be advantageous as an unimpeded light source outside receptacle 1 may negatively affect capturing images of receptacle 1, thus making the detection of isolated embryos more difficult.

Tray 3 is depicted as resting on a different surface 8. However, surface 5 and surface 8 may be part of a single surface. Furthermore, while surfaces 5 and 8 are depicted as being rectangular, other shapes are also possible.

Figure 5:
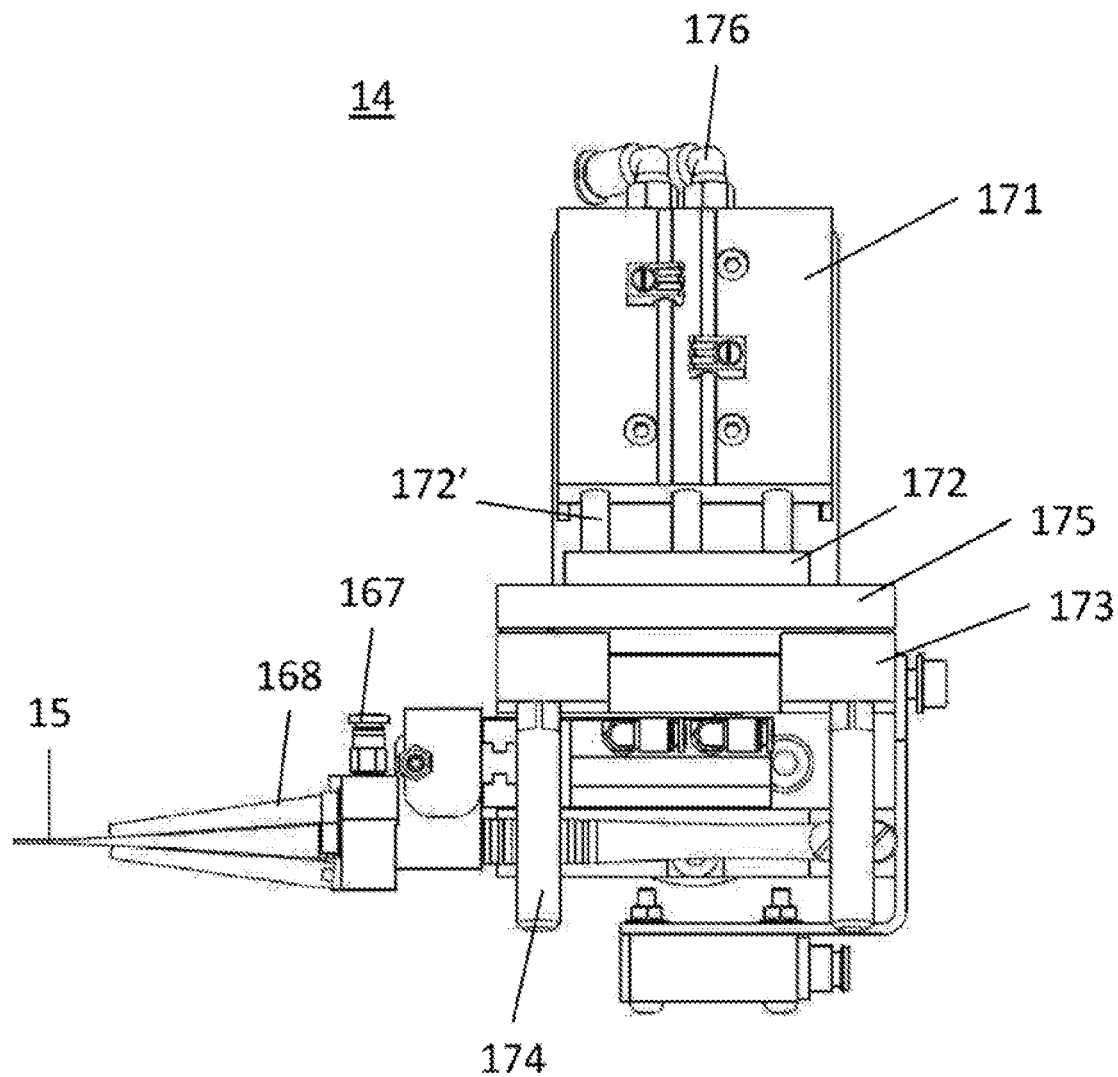
FIG. 5 is a side view of an embodiment of the pick-up unit according to the invention.

An embodiment of a system according to the invention may comprise a stationary frame relative to which surfaces 5 and 8 may have a fixed position. The system may further comprise a robotic arm 13 having a pick-up unit 14 mounted on an end thereof. Pick-up unit 14 may be provided with means for picking up a plant embryo, such as for instance tweezers 15. By means of robotic arm 13, pick-up unit 14 is able to translate and rotate to position itself relative to a piece of plant matter to be picked up. An example of a pick-up unit is illustrated in FIG. 5.

Robotic arm 13 and pick-up unit 14 are configured such that a plant embryo may be picked up from receptacle 1 from a position detected using an image made by an optical camera 12. Furthermore, robotic arm 13 may be controlled to position pick-up unit 14 such that the presence of a picked-up plant embryo may be checked above transparent region 2' in a second image made by camera 12. Robotic arm 13 may also be controlled to position pick-up unit 14 such that the plant embryo may be deposited in one of the compartments or test tubes 4 in tray 3 on surface 8.

Figure 3:
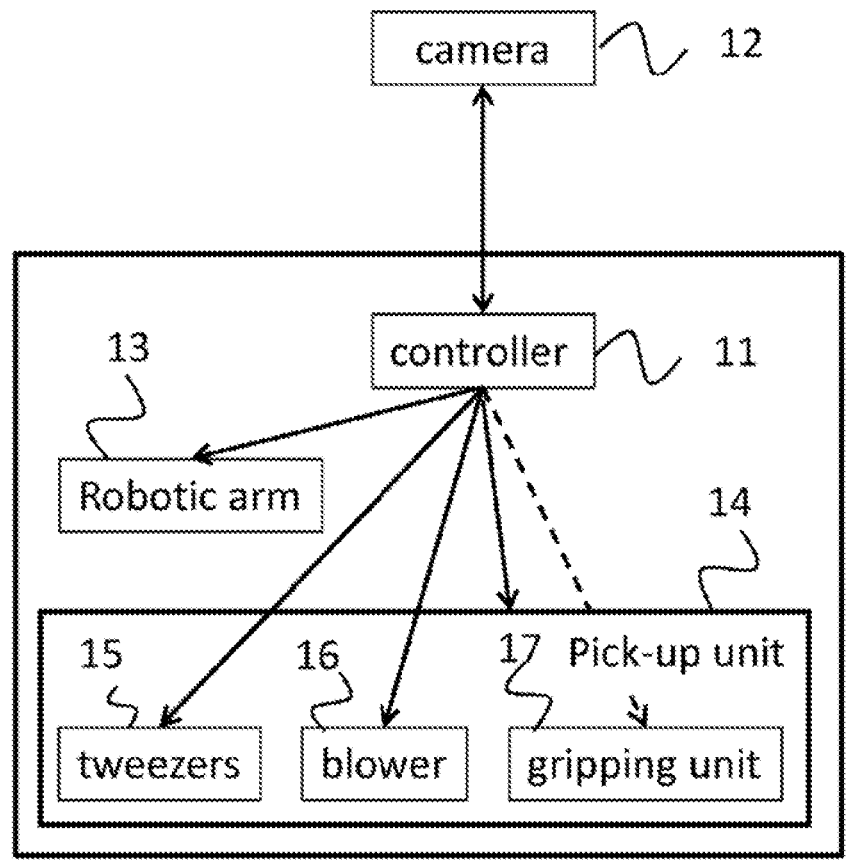
FIG. 3 is a block diagram of a system according to the invention.

FIG. 3 illustrates a block diagram of an embodiment of a system in accordance with the present invention. This system may comprise the components illustrated in FIGS. 1 and 2. Camera system 12 may comprise multiple cameras. Preferably, a single camera is used for capturing a first and second optical image. The camera(s) is/are preferably mounted to the stationary frame.

Robotic arm 13 and pick-up unit 14 are controlled by a controller 11, which may also control camera system 12 if needed. Based on the first and/or second optical image, controller 11 controls robotic arm 13 to move pick-up unit 14 to a desired position above first transparent region 2, which may be a position to pick-up an isolated embryo 6 of which the position and preferably also orientation have been determined in the first optical image. Controller 11 may also control robotic arm 13 to move pick-up unit 14 to a predetermined confirming position above second transparent region 2', or to a position above a compartment 4 in tray 3 in which a picked-up embryo may be deposited. Other positions may also be possible, such as for instance a position in which a gripping unit 17 may grip tray 3, a position to which tray 3 may be moved, and a position in which a new tray may be gripped by gripping unit 17. Gripping unit 17 may be incorporated in pick-up unit 14.

The position and orientation of pick-up unit 14 may be controlled by controller 11 indirectly by controlling robotic arm 13. Pick-up unit 14 may also be controlled directly by controller 11. For instance, a rotation of pick-up unit 14 may be controlled by controlling robotic arm 13 or by directly controlling pick-up unit 14. Robotic arms with pick-up units as well as methods to move these precisely are known from the prior art, and therefore the skilled person will be aware of several ways to control such a robotic arm and pick-up unit.

Pick-up unit 14 may comprise tweezers 15 suitable for picking up a plant embryo or other piece of plant matter. Tweezers 15 may be controlled by controller 11. For instance, tweezers 15 may be pneumatically actuated tweezers, and controller 11 may control the opening and closing of tweezers 15 by means of controlling one or more pneumatic cylinders. Controller 11 may also control a blower 16 which is part of a blowing unit, and which is preferably also part of pick-up unit 14. Pressurized gaseous medium such as air may be expelled by blower 16, for instance, from in between tweezers 15, in which case a small amount of gaseous medium may be expelled, if needed, to help with the depositing of the piece of plant matter into a compartment 4 in tray 3. Furthermore, the pneumatic actuation of tweezers 15 and the source of gaseous medium may be part of a single system. However, these latter options are not necessary. The skilled person will be able to assess in which circumstances this configuration would be useful.

While the word "gripping unit" suggests active gripping, and while controller 11 may control gripping unit 17 to grip tray 3, this need not be the case. Gripping unit 17 may also be embodied as a passive gripping unit, such as a hook or other gripping organ, which may cooperate with gravity in order to grip tray 3. In this latter case, controller 11 controlling robotic arm 13 and/or pick-up unit 14 may be sufficient to achieve gripping of tray 3.

Camera system 12 comprising at least one camera is used for capturing a first optical image which shows receptacle 1 and a second optical image for detecting a picked-up embryo. For instance, a single camera 12 may be affixed at a certain distance above surface 5. Camera 1$q$2 is preferably positioned such that it can capture an image on which both receptacle 1 and second transparent region 2' are visible without needing to be moved. However, while this is an efficient arrangement, the skilled person will be able to envisage alternate arrangements, for instance in which a single camera changes focus and/or position or in which several cameras are used.

Advantageously, it may be that in the second optical image, which allows the system to determine whether an embryo was indeed picked up, receptacle 1 is visible as well. If this is the case, and if the second optical image shows that no embryo was picked up, the location of a further isolated embryo may be detected from the second optical image as well, which allows pick-up unit 14 to pick-up a further embryo without either having to rely on the first optical image again (since the pick-up action may have changed the location of embryos) or requiring the capturing of a further first optical image. In other embodiments, when receptacle 1 is also captured in the second optical image, a single optical image may be used for both detecting isolated embryos 6 and for confirming the presence of a picked-up embryo held by tweezers 15.

Figure 4:
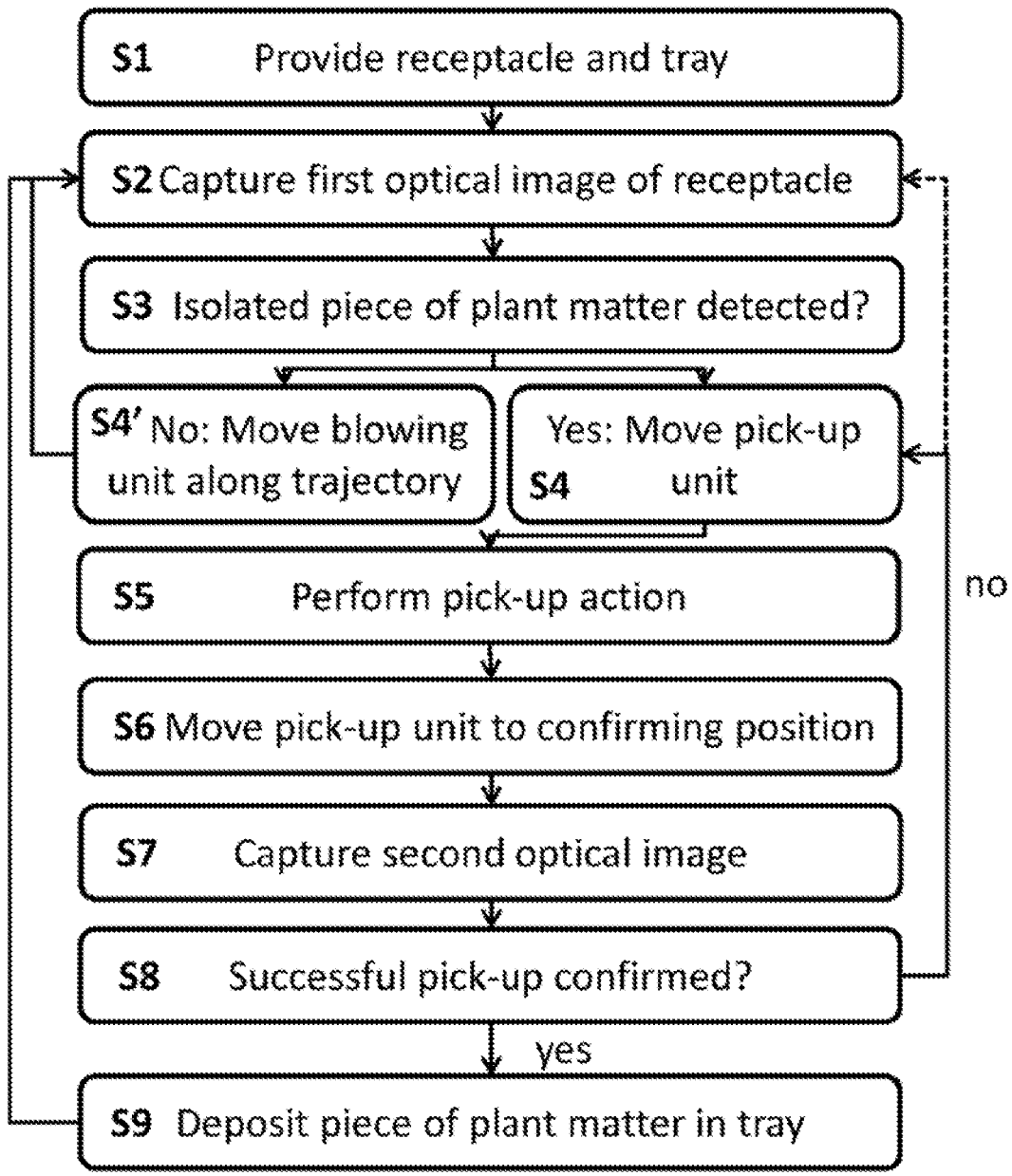
FIG. 4 is a flow chart illustrating a method in accordance with the invention.

FIG. 4 is a flowchart illustrating a method in accordance with the invention. More in particular, the method depicted in FIG. 4 can be used with the system depicted in FIG. 3.

In step S1, a receptacle and tray are provided. Both of these may be replaced while performing the method. The receptacle may be replaced once no more isolated embryos can be seen or blown loose from clusters, and the tray once there is an embryo in every compartment. While in the presently illustrated embodiment the replacement of the tray, by using a gripping unit which is attached to the pick-up unit, is automated and the replacement of the receptacle is not, replacing the tray may also be done manually and the process of replacing the receptacle may be automated as well. The skilled person will be able to determine, depending on circumstances and cost, which if any of these two processes to automate.

In step S2, a first optical image of the receptacle is captured. Preferably, the entire receptacle may be seen in this first optical image. To achieve this, the first optical image is preferably captured when the pick-up unit is away from the area between the camera capturing the first optical image and the receptacle itself.

In step S3, it is determined whether at least one isolated embryo may be seen in the first optical image. The skilled person will be familiar with algorithms which are able to do this, as detecting the presence of isolated embryos is known from the state of the art. To improve the accuracy of detection, the receptacle is preferably lighted from below as shown in FIG. 1, preferably by a light source which emits red light, for increased contrast.

The image of the isolated embryo may be compared with predetermined criteria, which may comprise features such as size, shape, colour. If the image of the embryo does not meet these criteria, the embryo may be discarded and a next isolated embryo is selected.

If at least one isolated embryo is detected in step S3, the pick-up unit is moved, in step S4, towards the receptacle, where it may be positioned above the location of the selected embryo. Once the pick-up unit is thus positioned, a pick-up action may be performed (S5), wherein for example tweezers close around the embryo and grab the embryo by its stem. To make this possible, it is advantageous to detect not just the presence and position of isolated embryos in the first optical image in step S3, but to also detect the orientation of a selected embryo. In step S4, the motion of the pick-up unit may not just serve to position it substantially above a selected embryo to be picked up, but may also comprise an element of rotation (of either the pick-up unit as a whole or just an element, e.g. the tweezers) to make it possible to pick-up the embryo in step S5.

Once the pick-up action has been performed, the pick-up unit may be moved, in step S6, to the predetermined confirming position above second transparent region 2' to confirm whether indeed an embryo was picked up in step S5. Advantageously, the pick-up unit is not just moved laterally for this step, but it rotated too, in such a way that a camera may get an unobstructed view of the position in which the embryo, if present, would be located. Generally, a rotation of the tweezers bringing the tweezers in an essentially horizontal plane should allow this. Next, a second optical image is captured in step S7. The light source improves accuracy, as the embryo, if present, will obstruct part of the light going from the light source to the camera. Therefore, the presence of an embryo may for instance be detected by determining if the shadow of an embryo is present in the second optical image captured in step S7.

The camera capturing the second optical image may be the same camera that captures the first optical image. In fact, the second optical image, which is taken as the pick-up unit is in the predetermined confirming position and hence is likely to not be obstructing the view of the receptacle from the camera, may also be used as the first optical image in a subsequent step S2. If necessary, however, a refocusing of the camera may take place between the capturing of the first optical image and the second optical image, in which case the second optical image will likely not be suited to be used as a subsequent first optical image. Separate cameras may also be used.

If a successful pick-up is confirmed in step S8, the pick-up unit may move towards the tray and deposit the embryo in a compartment of the tray. Various ways of achieving the depositing step will be familiar to the skilled person. If tweezers are used, simply opening the tweezers may be sufficient. Since the embryos may still have some medium attached to them and may therefore be sticky, a small blast of pressurized air may also be applied to deposit the embryo if necessary. After depositing the embryo in step S9, the method may be repeated by returning to step S2.

If the embryo is not detected in the second optical image in step S8, the pick-up unit is moved back to the receptacle in order to pick up a subsequent embryo in step S4. It may also be possible that the subsequent embryo is the same embryo which was not at first successfully picked up. The location of the embryo to be picked up may be detected from the second optical image. Alternately, the method may be repeated from step S2, and start with the capturing of a new first optical image, preferably before the pick-up unit is moved back, so as to obtain an unobstructed view of the receptacle.

Going back to step S3, if an isolated piece of plant matter such as a plant embryo is not detected in the first optical image, this may be because all embryos in the receptacle are clumped together in at least one cluster of embryos. To be able to deal with this, the system according to the invention may comprise a blowing unit, and in step S4' this blowing unit is moved along a first predefined trajectory while blowing a pressurized gaseous medium, e.g. air, downward toward the receptacle. This may break up at least one of the clusters to the extent that isolated embryos are again present in the receptacle. To see if the blowing unit moving along the predetermined trajectory had this desired result, a further first optical image of the receptacle may be captured, preferably after the blowing unit is moved to a position in which it does not impede the camera's view of the receptacle, and the presence of isolated embryos may be detected in this captured image. If an isolated embryo is detected, the process continues from step S4. If it is not, the blowing unit may be moved along a predetermined trajectory which is preferably different from the first predetermined trajectory, repeating step S4'. If after a certain number of repetitions of this process, for instance 3 repetitions, no isolated embryos are detected in the receptacle, the system may be configured to send a signal to a user, who may then replace the receptacle.

FIG. 5 and FIGS. 6A-6E show various views and cross sections of an embodiment of a pick-up unit according to the invention. In these figures, like reference numbers refer to like elements.

FIG. 5 is a front view of pick-up unit 14 that shows gripping unit 17 most clearly. The gripping unit may comprise a cylinder 171 which may move a piston 172 through actuation of piston rods 172'. Piston 172 is connected to a primary gripping element 175. Supporting elements 174 are also provided that are attached to secondary gripping elements 173. By actuating cylinder 171, piston 172 and primary gripping element 175 may be moved against secondary gripping elements 173, as seen in FIG. 6B, gripping an edge of a tray that is arranged in the space between elements 173, 175. In the shown embodiment, cylinder 171 is a pneumatic cylinder, controlled through air supply 176. Other means of actuating the gripping unit are of course also possible.

Figure 6A:
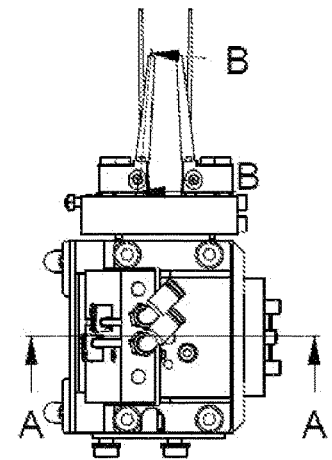
Figure 6B:
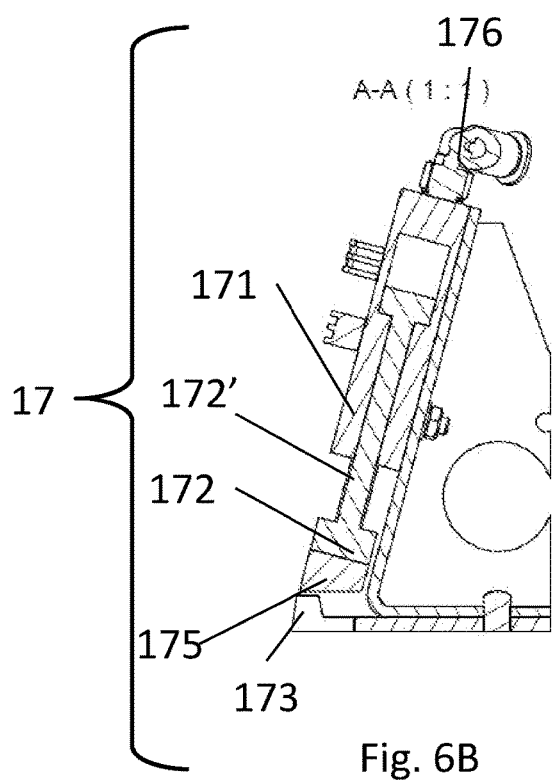
Figure 6C:
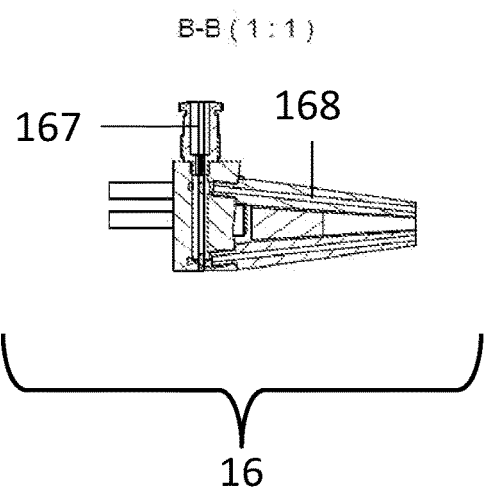

FIG. 6A shows a top view of pick-up unit 14. FIG. 6B shows a cross section through line A in FIG. 6A whereas FIG. 6C shows a cross section through line B. FIG. 6B shows a cross section through cylinder 171, piston 172, primary gripping element 172 and secondary gripping elements 173. An opening is visible between the primary and secondary gripping elements 173, 175 where the edge of a tray may be gripped.

FIG. 6C is a cross section of pick-up unit 14, specifically. More in particular, this figure shows air passages 168 through pick-up unit 15 that may be used either for the blowing function described above or, if needed, to deposit an embryo that is stuck to tweezers 15. Air may be supplied through air supply opening 167 and may then be blown through passages 168.

FIG. 6D is the same view as shown in FIG. 5. On it, a line C is indicated wherein FIG. 6E is a cross-section through this line. Air supply opening 167 for the pick-up unit is also indicated here, as are the elements comprising air passages 168. In this figure tweezers 15 which are used to pick up the embryo may also be seen.

FIG. 6E is a cross section in which the operation of tweezers 15 may be seen in more detail. Tweezers 15 in this embodiment are pneumatically actuated by means of a double-acting cylinder 150, though alternatives are also possible. Air supply channels 151 and 152 may be used to close and open tweezers 15, respectively, by supplying a suitable pressurized gaseous medium.

A setting screw 155 is shown that allows the positioning of supporting blocks 153, 154. The space between blocks 153, 154 determines the maximum angle or stroke of tweezers 15.

The embodiment described above is included only for illustrative purposes. The skilled person will be able to envisage equivalents for many of the above-mentioned features, and the scope of the claims is not limited to the specific features mentioned above.

Although the present invention and its advantages have been described in detail, it should be understood that various changes, substitutions and alterations can be made herein without departing from the spirit and scope of the invention as defined in the appended claims.

The invention is further described by the following numbered paragraphs:

1. A method for picking up and collecting plant matter, in particular plant embryos, comprising the following steps:
   capturing a first optical image being an image of at least one piece of plant matter, such as a plant embryo, arranged in a receptacle;
   detecting an isolated piece of plant matter in the captured first optical image; controlling a robotic arm having a pick-up unit mounted thereon to move the pick-up unit to a position in which it is able to pick up the isolated piece of plant matter;
   performing a picking up action for picking up the isolated piece of plant matter using the pick-up unit;
   controlling the robotic arm to move the pick-up unit to a predefined confirming position,
   capturing a second optical image in which a part associated with the picked-up piece of plant matter does not overlap with a part, if any, that is associated with the receptacle;
   controlling the robotic arm to move the pick-up unit to deposit the picked up piece of plant matter in a respective compartment in a tray comprising at least one compartment, if the picked up piece of plant matter is visible in the second optical image, or controlling the robotic arm to move the pick-up unit to a position in which it is able to pick up a further isolated piece of plant matter, if no picked up piece of plant matter is visible in the second optical image.
2. The method according to paragraph 1, wherein the receptacle is visible in the second optical image, the method further comprising detecting the further isolated piece of plant matter from the second optical image.
3. The method according to paragraph 1, comprising detecting the further isolated piece of plant matter from the first optical image.
4. The method according to any one of the previous paragraphs, comprising capturing a new first optical image for detection of a piece of plant matter to be picked up next when the pick up unit does not obstruct a view of the receptacle in the new first optical image.
5. The method according to paragraph 4, wherein said new first optical image is captured when the pick-up unit is at or moving towards the position for depositing a picked-up piece of plant matter.
6. The method according to any of the previous paragraphs, comprising using a same optical camera for obtaining the first and second optical images.
7. The method according to paragraph 6, wherein the optical camera performs a zooming function prior to recording the second optical image.
8. The method according to any of the previous paragraphs, wherein said detecting an isolated piece of plant matter or said detecting a further isolated piece of plant matter comprises:
   finding an isolated piece of plant matter in the first or second optical image;
   comparing at least one of a size, colour, and shape to predetermined criteria;
   determining that the isolated piece of plant matter should be picked up if said at least one of a size, an orientation, colour, and shape meets the predetermined criteria.
9. The method according to one of the previous paragraphs, comprising controlling the robotic arm to rotate the pick-up unit during and/or after a movement to the predefined confirming position, to allow a better view of the picked-up piece of plant matter, if present.
10. The method according to one of the previous paragraphs, additionally comprising a step of detecting an orientation of the isolated piece of plant matter or the further isolated piece of plant matter in the first and/or second optical image, and orienting the pick-up unit accordingly prior to performing the picking up action.
11. The method according to one of the previous paragraphs, comprising, if no isolated piece of plant matter is detected in the first and/or second optical image, moving a blowing unit along a pre-set trajectory while directing a pressurized gaseous medium, such as air, toward the receptacle.
12. The method according to paragraph 11, comprising, after the step of moving the blowing unit along a pre-set trajectory,
   moving the blowing unit to a position wherein a new first or second optical image can be obtained having a substantially unobstructed view of the receptacle; and
   detecting whether there are any isolated pieces of plant matter in the receptacle using the first and/or second optical image.
13. The method according to paragraph 12, further comprising, if no isolated pieces are detected in the last step, moving the blowing unit along a different pre-set trajectory while directing the pressurized gaseous medium toward the receptacle.
14. The method according to any of paragraphs 11-13, comprising, if no isolated pieces are detected, a step of transmitting a warning signal to an operator.
15. The method according to any of paragraphs 11-14, wherein the step of directing pressurized gaseous medium toward the receptacle involves blowing the pressurized gaseous medium downward at a substantially straight angle with respect to a plan defined by the bottom of the receptacle.
16. The method according to any of the previous paragraphs, comprising, once there are no longer any free compartments in the tray, replacing the tray.
17. The method according to paragraph 17, using a gripping unit for replacing the tray.
18. The method according to any of the paragraphs, wherein the blowing unit and/or the gripping unit are mounted to the same robotic arm as the pick-up unit, and wherein the movement of the blowing unit and/or gripping unit is controlled by controlling the robotic arm.

19. A system for picking up plant matter and for collecting the picked-up plant matter in a tray having at least one compartment, in particular plant embryos, comprising:
a surface whereupon a receptacle containing at least one piece of plant matter such as a plant embryo may be provided;
a robotic arm provided with a pick-up unit configured to pick-up a piece of plant matter, wherein the robotic arm is able to move the pick-up unit for picking up a piece of plant matter from the receptacle, to move the pick-up unit a predefined confirming position for confirming the picking up of a piece of plant matter, and to move the pick-up unit for depositing a picked-up piece of plant matter into a tray comprising at least one compartment suitable for receiving the picked-up piece of plant matter;
a camera system comprising an optical camera, said system being configured for capturing a first optical image being an image of at least one piece of plant matter arranged in a receptacle, and for capturing a second optical image in which a part associated with the picked-up piece of plant matter does not overlap with a part, if any, that is associated with the receptacle; and
a controller configured for:
detecting an isolated piece of plant matter in the first optical image;
controlling the robotic arm to move the pick-up unit to a position in which the unit can pick-up the detected isolated piece of plant matter;
controlling the pick-up unit to pick-up the detected isolated piece plant matter;
controlling the robotic arm to move the pick-up unit to a predefined confirming position;
confirming the presence of a picked-up piece of plant matter in the second optical image;
controlling the robotic arm and the pick-up unit to deposit the picked up piece of plant matter in a respective compartment if the picked up piece of plant matter is visible in the second optical image, or controlling the robotic arm to move the pick-up unit to a position in which it is able to pick up a further isolated piece of plant matter if no picked up piece of plant matter is visible in the second optical image.

20. The system according to paragraph 19, further comprising a first light source configured for emitting light through the surface from a side of the surface opposite to a side of the surface where the receptacle is or is to be placed, wherein the receptacle is provided between the camera system and the light source, said light source preferably emitting red light.

21. The system according to paragraph 19 or 20, further comprising a second light source, wherein the pick-up unit, when at the predefined confirming position, is located between the camera system and a second light source that is configured for emitting light to the pick-up unit, said light source preferably emitting red light.

22. The system according to paragraph 20 or 21, wherein the first light source is the second light source.

23. The system according to one of the paragraphs 20-22, wherein the surface comprises a first transparent region on which the receptacle is to be placed and a second transparent region, spaced apart from the first transparent region, wherein the first light source is configured for emitting light through the first transparent region, and wherein the second light source is configured for emitting light through the second transparent region.

where the light source is embodied as a lighted surface covered by a mask with two windows, wherein one of the windows is substantially the same size as the receptacle and the receptacle is provided thereon.

24. The system according to one of the previous paragraphs, wherein the pick-up unit comprises a pair of tweezers suitable for picking up an isolated piece of plant matter, wherein the tweezers are part of the pick-up unit.

25. The system according to paragraph 24, wherein the tweezers are pneumatically actuated tweezers.

26. The system according to any of paragraphs 19-25, further comprising a blowing unit suitable for directing a pressurized gaseous medium at the receptacle, wherein the blowing unit is preferably controlled by the controller.

27. The system according to any of paragraphs 19-26, further comprising a gripping unit suitable for gripping the tray, wherein the gripping unit is preferably controlled by the controller.

28. The system according to paragraph 26 or 27, wherein the blowing unit and/or the gripping unit are mounted to the same robotic arm as the pick-up unit, and wherein the movement of the blowing unit and/or gripping unit is controlled by controlling the robotic arm, and/or wherein the blowing unit and/or the gripping unit are incorporated in the pick-up unit.

29. A pick-up unit being configured as the pick-up unit defined in any of the paragraphs 19-28.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:
1. A method for picking up and collecting plant matter comprising the following steps:
capturing a first optical image being an image of at least one piece of plant matter arranged in a receptacle;
detecting an isolated piece of plant matter in the captured first optical image;
controlling a robotic arm having a pick up unit mounted thereon to move the pick up unit to a position in which it is able to pick up the isolated piece of plant matter;
performing a picking up action for attempting to pick up the isolated piece of plant matter using the pick up unit;
controlling the robotic arm to move the pick up unit to a predefined confirming position, capturing a second optical image in which a part associated with the picked up piece of plant matter does not overlap with a part, if any, that is associated with the receptacle; and
detecting that no picked up piece of plant matter is visible in the second optical image and controlling the robotic arm to move the pick up unit to a position in which it is able to pick up a further isolated piece of plant matter; the method further comprising:
moving a blowing unit along a pre-set trajectory while directing a pressurized gaseous medium, such as air, toward the receptacle if no isolated piece of plant matter is detected in the first and/or second optical image, wherein the blowing unit comprises an air supply opening and passages through the pick up unit, wherein air supplied through the air supply opening is blown through the passages, and wherein the movement of the blowing unit is controlled by controlling the robotic arm.

2. The method according to claim 1, wherein the receptacle is positioned to be visible in the second optical image, the method further comprising detecting the further isolated piece of plant matter from the second optical image, or the method further comprising detecting the further isolated piece of plant matter from the first optical image.

3. The method according to claim 1, comprising capturing a new first optical image for detection of a piece of plant matter to be picked up next when the pick up unit does not obstruct a view of the receptacle in the new first optical image, wherein said new first optical image is captured when the pick up unit is at or moving towards the position for depositing a picked up piece of plant matter.

4. The method according to claim 1, comprising using a same optical camera for obtaining the first and second optical images, wherein the optical camera performs a zooming function prior to recording the second optical image.

5. The method according to claim 1, wherein said detecting an isolated piece of plant matter or said detecting a further isolated piece of plant matter comprises:

finding an isolated piece of plant matter in the first or second optical image;

comparing at least one of a size, color, and shape to predetermined criteria;

determining that the isolated piece of plant matter should be picked up if said at least one of a size, an orientation, color, and shape meets the predetermined criteria.

6. The method according to claim 1, comprising controlling the robotic arm to rotate the pick up unit during and/or after a movement to the predefined confirming position, to allow a better view of the picked up piece of plant matter, if present.

7. The method according to claim 1, additionally comprising a step of detecting an orientation of the isolated piece of plant matter or the further isolated piece of plant matter in the first and/or second optical image, and orienting the pick up unit accordingly prior to performing the picking up action.

8. The method according to claim 1, comprising, after the step of moving the blowing unit along a pre-set trajectory, moving the blowing unit to a position wherein a new first or second optical image can be obtained having a substantially unobstructed view of the receptacle; and detecting whether there are any isolated pieces of plant matter in the receptacle using the first and/or second optical image;

the method further comprising, in response to detecting that no isolated pieces are in the receptable in the last step, moving the blowing unit along a different pre-set trajectory while directing the pressurized gaseous medium toward the receptacle.

9. The method according to claim 1, comprising, if no isolated pieces are detected, a step of transmitting a warning signal to an operator, and/or wherein the step of directing pressurized gaseous medium toward the receptacle involves blowing the pressurized gaseous medium downward at a substantially straight angle with respect to a plane defined by the bottom of the receptacle.

10. The method according to claim 1, comprising, once there are no longer any free compartments in the tray, replacing the tray with a gripping unit;

wherein the gripping unit comprises a primary gripping element and a secondary gripping element mounted to the same robotic arm as the pick up unit and movable with respect to each other when actuated;

wherein the movement of the primary and/or second gripping elements with respect to each other is controlled by controlling the robotic arm.

11. A system for picking up plant matter and for collecting the picked up plant matter in a tray having at least one compartment comprising:

a surface whereupon a receptacle containing at least one piece of plant matter such as a plant embryo may be provided;

a robotic arm provided with a pick up unit configured to pick up a piece of plant matter, wherein the robotic arm is able to move the pick up unit for picking up a piece of plant matter from the receptacle, to move the pick up unit a predefined confirming position for confirming the picking up of a piece of plant matter, and to move the pick up unit for depositing a picked up piece of plant matter into a tray comprising at least one compartment suitable for receiving picked up piece of plant matter;

a camera system comprising an optical camera, said system being configured for capturing a first optical image being an image of at least one piece of plant matter arranged in a receptacle, and for capturing a second optical image in which a part associated with the picked up piece of plant matter does not overlap with a part, if any, that is associated with the receptacle;

a controller configured for:

detecting an isolated piece of plant matter in the first optical image;

controlling the robotic arm to move the pick up unit to a position in which the unit can pick up the detected isolated piece of plant matter;

controlling the pick up unit to perform a picking up action for attempting to pick up the detected isolated piece plant matter;

controlling the robotic arm to move the pick up unit to a predefined confirming position;

confirming the presence of a picked up piece of plant matter in the second optical image; and detecting that no picked up piece of plant matter is visible in the second optical image and controlling the robotic arm to move the pick up unit to a position in which it is able to pick up a further isolated piece of plant matter;

and a blowing unit suitable for directing a pressurized gaseous medium at the receptacle, wherein the blowing unit is controlled by the controller, wherein the blowing unit comprises an air supply opening and passages through the pick up unit, wherein air supplied through the air supply opening is blown through the passages, and wherein the movement of the blowing unit is controlled by controlling the robotic arm;

wherein the pick up unit comprises a pair of tweezers suitable for picking up an isolated piece of plant matter, said tweezers being part of the pick up unit, and wherein the tweezers are pneumatically actuated tweezers.

12. The system according to claim 11, further comprising:

a first light source configured for emitting light through the surface from a side of the surface opposite to a side of the surface where the receptacle is or is to be placed, wherein the receptacle is provided between the camera system and the light source; and/or a second light source, wherein the pick up unit, when at the predefined confirming position, is located between the camera system and a second light source that is configured for emitting light to the pick up unit.

13. The method of claim 1, wherein the plant matter is a plant embryo.

14. The system of claim 11, wherein the plant matter is a plant embryo.

15. The system according to claim 12, wherein the surface comprises a first transparent region on which the receptacle is to be placed and a second transparent region, spaced apart from the first transparent region, wherein the first light source is configured for emitting light through the first transparent region, wherein the second light source is configured for emitting light through the second transparent region, and wherein the first light source and the second light source emit red light.

16. The system according to claim 11, further comprising a lighted surface covered by a mask with two windows, in which one of the windows is substantially the same size as the receptacle and the receptacle is provided thereon, and the other window is located such that the pick up unit, when at the predefined confirming position, is located between the camera system and said other window, wherein the lighted surface emits red light through the two windows.

17. The system according to claim 11, further comprising a gripping unit suitable for gripping the tray, wherein the gripping unit is controlled by the controller, wherein the gripping unit comprises a primary gripping element and a secondary gripping element mounted to the same robotic arm as the pick up unit and movable with respect to each other when actuated, and wherein the movement of the primary and/or secondary gripping elements with respect to each other is controlled by controlling the robotic arm.

\* \* \* \* \*